| United States Patent [19] | [11] Patent Number: 4,599,306 |
| --- | --- |
| Altrock | [45] Date of Patent: Jul. 8, 1986 |

[54] MONOCLONAL ANTIBODIES WHICH SPECIFICALLY BIND TO HUMAN IMMUNE INTERFERON

[75] Inventor: Bruce W. Altrock, Moorpark, Calif.

[73] Assignee: AMGEN, Thousand Oaks, Calif.

[21] Appl. No.: 485,205

[22] Filed: Apr. 15, 1983

[51] Int. Cl.$^4$ ............ G01N 53/00; C12N 15/00; C12N 5/00
[52] U.S. Cl. .................... 435/7; 435/68; 435/172.2; 435/240; 436/518; 436/536; 436/548; 935/104; 935/108; 935/110; 350/351; 350/413
[58] Field of Search ............ 435/4, 7, 68, 811, 948, 435/172.2, 70, 172, 240; 436/547, 548, 804, 518, 536; 260/112 R; 935/104, 108, 110

[56] References Cited

U.S. PATENT DOCUMENTS

| | | | |
| --- | --- | --- | --- |
| 4,252,791 | 2/1981 | Grossberg et al. | 260/112 R |
| 4,285,929 | 8/1981 | Sugimoto et al. | 424/85 |
| 4,289,690 | 9/1981 | Pestka et al. | 260/112 R |
| 4,296,025 | 10/1981 | Sugimoto | 260/112 R |
| 4,311,639 | 1/1982 | Ganfield | 260/112.5 R |
| 4,341,761 | 7/1982 | Ganfield et al. | 260/112.5 R |
| 4,362,155 | 12/1982 | Skurkovich et al. | 604/6 |
| 4,376,821 | 3/1983 | Braude | 435/68 |
| 4,376,822 | 3/1983 | Braude | 435/68 |
| 4,382,027 | 5/1983 | Braude | 260/112 R |
| 4,420,398 | 12/1983 | Castino | 210/641 |
| 4,423,147 | 12/1983 | Secher et al. | 435/68 |

FOREIGN PATENT DOCUMENTS

| | | |
| --- | --- | --- |
| 0103898 | 3/1984 | European Pat. Off. . |
| 3200657 | 2/1983 | Fed. Rep. of Germany . |
| 2092614 | 8/1982 | United Kingdom . |

OTHER PUBLICATIONS

Staehelin, T. et al., J. Biological Chemistry, vol. 256, pp. 9750–9754 (1981).
Maeda, S. et al., Proc. Natl. Acad. Sci. USA, vol. 77 (12), pp. 7010–7013 (12-1980).
Valibracht, A. et al., Nature, vol. 289, pp. 496–497 (2-1981).
Stefanos, S. et al., J. General Virology, vol. 50 (1), pp. 225–229 (1980).
Oleszak, E. et al., Hybridoma, vol. 2(4), pp. 439–449 (12-1983): Oral Disclosure, Nov. 1, 1982, see p. 448.
Meurs, E. et al., Infection and Immunity, vol. 37 (3), pp. 919–926 (9-1982) mcαhuαIF.
Secher, D. S., Nature, vol. 290, pp. 501–503, (4-1981).
Langford, M. P. et al., J. Immunology, vol. 126 (4), pp. 1620–1623 (4-1981).
Rubin, B. Y. et al., Journal of Immunology, vol. 130, pp. 1019–1020 (Mar. 1983).
Osborn, J. C., IRCS Med. Sci: Libr. Compend., vol. 8 (4), p. 212 (1980).
Alton, K. et al., Biol. Interferon Sep., Proc. Int., De Maeyer et al., ed., pp. 119–128 (1983), Elsevier, Netherlands.
Spitalny, G. J., J. Exp. Med., vol. 159(5), pp. 1560–1565 (1984).
Altrock, B. et al., Biol. Interferon, Syst. Proc. Int., De Maeyer et al., ed., pp. 135–138 (1983), Elsevier, Netherlands.
De Maeyer, E. et al., ed., The Biology of the Interferon System, Elsevier, Amsterdam (1983).
Hochkeppel, H. K. et al., Nature, vol. 296, pp. 258–259 (1982).
Yip, Y. K. et al., Proc. Natl. Acad. Sci. USA, vol. 79, pp. 1820–1825 (1982).
Yip, Y. P. et al., Science, vol. 245, pp. 411–412, (1982).
Le, J. et al., J. Immunological Methods, vol. 69 (1), pp. 61–70 (1984).
Le, J. et al. J. Immunology, vol. 132(3), pp. 1300–1304 (1984).
Novick, D. et al., Embo. Journal, vol. 2(9), pp. 1527–1530 (1983).
Johnson, H. M. et al., J. Immunology, vol. 129(6), pp. 2357–2359 (1982).
Baron et al., *Cell*, 28: 395–404 (1982).
Burnett, *Anal. Biochem.*, 112: 195–203 (1981).
Chisholm, *High Technology*, 3(1): 57–63 (1983).
Dreesman et al., *Nature*, 295: 158–160 (1982).
Edge et al., *Nature*, 292: 756–782 (1981).
Goding, *J. Imm. Methods*, 39: 285–308 (1980).
Gray et al., *Nature*, 295: 503–508 (1982).
Green et al., *Cell*, 28: 477–487 (1982).
Hopp et al., *PNAS (USA)*, 78: 3824–3828 (1981).
Hunter et al., *Nature*, 194: 495–496 (1962).
Imai et al., *J. Immunology*, 128: 2824–2825 (1982).
Lerner et al., *Cell*, 23: 309–310 (1981).

(List continued on next page.)

*Primary Examiner*—Thomas G. Wiseman
*Assistant Examiner*—M. Moskowitz
*Attorney, Agent, or Firm*—Marshall, O'Toole, Gerstein, Murray & Bicknell

[57] ABSTRACT

Disclosed are monoclonal antibody substances specifically immunologically reactive with native and recombinant human immune interferon ("IFN-γ") and with polypeptides having amino acid sequences substantially duplicative of sequences extant in IFN-γ. In a presently preferred embodiment, antibody substances are produced by new mouse-mouse hybridoma tumor cell line A.T.C.C. HB 8291 and are immunoreactive with native IFN-γ, with recombinant IFN-γ and polypeptide analogs thereof, and with a nonadecapeptide whose amino acid sequence duplicates that of the final nineteen amino acid residues of the carboxyl terminal of IFN-γ. These preferred antibody substances, while displaying high affinity for IFN-γ, do not neutralize antiviral biological activity of the interferon. They are usefully employed in the detection, quantification and affinity purification of IFN-γ and IFN-γ analogs as well as in investigations relating to the mode of biological action of IFN-γ.

4 Claims, No Drawings

OTHER PUBLICATIONS

Lerner et al., *PNAS (USA)*, 78: 3403–3407 (1981).
Lerner, *Scientific American*, 248(2): 66–74 (1983).
Merrifield, *J. Amer. Chem. Soc.*, 85: 2149–2154 (1963).
Nigg et al., *PNAS (USA)*, 79: 5322–5326 (1982).
Oi et al., pp. 351–372, in *Selected Methods in Cellular Immunology*, (Mishell et al., eds.), W. H. Freeman Publishing, San Francisco (1979).
Ross et al., *Nature*, 294: 654–656 (1981).
Shulman et al., *Nature*, 276: 269–279 (1978).
Secher et al., *Nature*, 285: 446–450 (1980).
Staehelin et al., *PNAS*, 78: 1848–1852 (1981).
Todd et al., *T.I.B.S.*, 7: 212–216 (1982).
Walter et al., *PNAS (USA)*, 77: 5197–5200 (1980).
Walter et al., *PNAS (USA), 78: 4882–4886 (1981)*.
Wong et al., *PNAS (USA)*, 78: 7412–7416 (1981).

MONOCLONAL ANTIBODIES WHICH SPECIFICALLY BIND TO HUMAN IMMUNE INTERFERON

BACKGROUND OF THE INVENTION

The present invention relates generally to materials and methods useful in the quantitative detection and affinity purification of human immune interferon ("IFN-γ") and structurally related polypeptides such as analogs of INF-γ produced by recombinant methods.

Of substantial interest to the background of the present invention is the state of the art with regard to the preparation and use of a class of biologically active substances, the interferons (IFNs). Interferons are secreted proteins having fairly well-defined antiviral, antitumor and immunomodulatory characteristics. See, e.g., Gray, et al., Nature, 295, pp. 503-508 (1982) and Edge, et al., Nature, 292, pp. 756-782 (1981), and references cited therein.

On the basis of antigenicity and biological and chemical properties, human interferons have been grouped into three major classes: IFN-α (leukocyte), IFN-β (fibroblast) and IFN-γ (immune). Considerable information has accumulated on the structures and properties of the virus-induced acid-stable interferons (IFN-α and β ). These have been purified to homogeneity and at least partial amino acid sequences have been determined. Analyses of cloned cDNA gene sequences for IFN-β and the IFN-α multigene family have permitted the deduction of the complete amino acid sequences of many of the interferons. In addition, efficient synthesis of IFN-β and several IFN-αs in E. coli, and subtype IFN-α₁, in yeast, have now made possible the purification of large quantities of these proteins in biologically active form.

Much less information is available concerning the structure and properties of IFN-γ, an interferon generally produced in cultures of lymphocytes exposed to various mitogenic stimuli. It is acid labile and does not cross-react with antisera prepared against IFN-α or IFN-β. A broad range of biological activities have been attributed to IFN-γ including potentiation of the antiviral activities of IFN-α and -β from which it differs in terms of its virus and cell specificities and the antiviral mechanisms induced. In vitro studies performed with crude preparations suggest that the primary function of IFN-γ may be as an immunoregulatory agent. The antiproliferative effect of IFN-γ on transformed cells has been reported to be 10 to 100-fold greater than that of IFN-α or -β, suggesting a potential use in the treatment of neoplasia. Murine IFN-γ preparations have been shown to have significant antitumor activity against mouse sarcomas.

It has recently been reported (Gray, et al., supra) that a recombinant plasmid containing a cDNA sequence coding for human IFN-γ has been isolated and characterized. Expression of this sequence in E. coli and cultured monkey cells is reported to give rise to a polypeptide having the properties of authentic human IFN-γ. In the publication, the deduced 146 amino acid sequence of the "mature" polypeptide, exclusive of the putative leader sequence, is as follows:

```
1                                           10
Cys—Tyr—Cys—Gln—Asp—Pro—Tyr—Val—Lys—Glu—
```
-continued
```
—Ala—Glu—Asn—Leu—Lys—Lys—Tyr—Phe—Asn—

20
—Ala—Gly—His—Ser—Asp—Val—Ala—Asp—Asn—

30
—Gly—Thr—Leu—Phe—Leu—Gly—Ile—Leu—Lys—

40
—Asn—Trp—Lys—Glu—Glu—Ser—Asp—Arg—Lys—

50
—Ile—Met—Gln—Ser—Gln—Ile—Val—Ser—Phe—

60
—Tyr—Phe—Lys—Leu—Phe—Lys—Asn—Phe—Lys—

70
—Asp—Asp—Gln—Ser—Ile—Gln—Lys—Ser—Val—

80
—Glu—Thr—Ile—Lys—Glu—Asp—Met—Asn—Val—

90
—Lys—Phe—Phe—Asn—Ser—Asn—Lys—Lys—Lys—

100
—Arg—Asp—Asp—Phe—Glu—Lys—Leu—Thr—Asn—

—Tyr—Ser—Val—Thr—Asp—Leu—Asn—Val—Gln—

110
—Arg—Lys—Ala—Ile—His—Glu—Leu—Ile—Gln—

120
—Val—Met—Ala—Glu—Leu—Ser—Pro—Ala—Ala—

130
—Lys—Thr—Gly—Lys—Arg—Lys—Arg—Ser—Gln—

140                      146
—Met—Leu—Phe—Gln—Gly—Arg—Arg—Ala—Ser—Gln
```

In a previous publication of the sequence, arginine, rather than glutamine, was specified at position 140 in the sequence. (Unless otherwise indicated, therefore, reference to "human immune interferon" or, simply "IFN-γ" shall comprehend both the [Arg¹⁴⁰] and [Gln¹⁴⁰] forms.)

The above-noted wide variations in biological activities of various interferon types makes the construction of synthetic polypeptide analogs of the interferons of paramount significance to the full development of the therapeutic potential of this class of compounds. Co-owned, co-pending U.S. patent application Ser. No. 375,494 by Alton, et al., filed May 6, 1982, relates to procedures for the rapid manufacture of structural genes specifying human interferons and analogs thereof and to the use of these manufactured genes to secure microbial expression of biologically active polypeptide products.

Of substantial interest to the background of the invention is the extensive body of information generated over the recent past with respect to the use of immunological procedures for the isolation and quantitative detection of complex, biologically active polypeptides such as the inteferons. Such immunological procedures have frequently employed polyclonal, serum-derived antibodies directed against the proteinaceous materials of interest. Briefly put, antisera and serum-derived antibodies are obtained by inoculation of an immunologically-active animal, such as a rat or rabbit, with the material of interest. The injected material is recognized as a foreign antigenic substance by the immune system of the animal and elicits production of antibodies against the antigen. Differing cells responding to stimulation by the antigenic substance produce and release into circulation antibodies slightly different from those produced by other responding cells. The antibody activity remains in the serum of the animal when its blood is extracted. While unpurified serum or antibody preparations purified as serum immunoglobulin fractions may then be used in assays to detect and complex with the proteinaceous material in fluids and on gels, the antibody preparations suffer from a major disadvantage. Serum antibodies, composed of all the different antibodies produced by individual cells, are polyclonal in nature and for the most part are reactive with antigens other than the one of interest. Antibodies specific for the desired product represent a subset of the antibodies present in serum.

Of interest to the background of the present invention are recent advances in the art of developing continuous cultures of cells capable of producing a single species of antibody (a "monoclonal" antibody) which is specifically immunologically reactive with a single antigenic determinant of a selected antigen. See, generally, Chisholm, *High Technology*, Vol. 3, No. 1, 57–63 (1983) and Todd, et al., *T.I.B.S.*, 7, pp. 212–216 (1982). Monoclonal antibodies have proven to be invaluable for the characterization, quantitative analysis, and purification of macromolecular antigens, including such biologically active compounds as leukocyte interferons. See generally, Secher, et al., *Nature*, 285, pp. 446–450 (1980); Staehelin, et al., *P.N.A.S*, 78, pp. 1848–1852 (1981); and Imai, et al., *J.Immunology*, 128, pp. 2824–2825 (1982). The lack of availability of monoclonal antibodies to IFN-γ is becoming a more pronounced problem in view of the above-noted advances in the capacity to employ recombinant methods for the production of IFN-γ and its analogs. Antibodies with high specific affinity for these substances would not only be useful for purification of IFN-γ and analogs thereof from microbial production systems, but would also be useful in quantitative analytical methods involving IFN-γ. For example, such antibody preparations would be useful in the characterization of cell surface receptors for IFN-γ (including their distribution and modulation) and in characterizing the receptor binding qualities of IFN-γ analogs. Such information, in turn, would have clinical diagnostic and therapeutic significance in interferon management of disease.

Also of interest to the background of the invention are reports of the immunological activity of synthetic peptides which substantially duplicate the amino acid sequence extant in naturally-occurring proteins, glycoproteins and nucleoproteins. More specifically, relatively low molecular weight polypeptides have been shown to participate in immune reactions which are similar in duration and extent to the immune reactions of physiologically significant proteins such as viral antigens, polypeptide hormones and the like. Included among the immune reactions of such polypeptides is the provocation of the formation of specific antibodies in immunologically active animals. See, e.g., Lerner, et al., *Cell*, 23, 309–310 (1981); Ross, et al., *Nature*, 294, 654–656 (1981); Walter, et al., *P.N.A.S. (U.S.A.)*, 77, 5197–5200 (1980); Lerner, et al., *P.N.A.S. (U.S.A.)*, 78, 3403–3407 (1981); Walter, et al., *P.N.A.S. (U.S.A.)*, 78, 4882–4886 (1981); Wong, et al., *P.N.A.S. (U.S.A.)*, 78, 7412–7416 (1981); Green, et al., *Cell*, 28, 477–487 (1982); Nigg, et al., *P.N.A.S. (U.S.A.)*, 79, 5322–5326 (1982); Baron, et al., *Cell*, 28, 395–404 (1982); Dreesman, et al., *Nature*, 295, 158–160 (1982); and Lerner, *Scientific American*, 248, No. 2, 66–74 (1983).

The advantages of antibody preparations immunoreactive with both a macromolecule and with a readily available synthetic peptide are manifest. Co-owned, co-pending U.S. patent application Ser. No. 463,724, by Egrie, filed Feb. 4, 1983 discloses the development and use of monoclonal antibodies which are both immunologically reactive with human erythropoietin and reactive with a synthetic polypeptide which is duplicative of an amino acid sequence determined to be extant in erythropoietin. This achievement is indeed a rare one, owing to the fact that polypeptide fragments in solutions employed as inoculants cannot ordinarily be expected to assume an "antigenic" configuration similar to that which the polypeptide sequence naturally assumes as part of a macromolecular material. Consequently, monoclonal antibodies to whole macromolecules seldom bind peptide fragments well, and vice versa.

To date, there have been no published reports of the development of monoclonal antibodies, raised against interferon peptide fragments, and which have high affinity for interferon-duplicating peptide fragments and high affinity for native interferon species. It has quite recently been reported that polyclonal antibody preparations have been raised in rabbits in response to administration of a synthetic peptide corresponding to the first 20 amino acids of the amino (N) terminal of IFN-γ. [Johnson, et al., *J. Immunology*, 129, pp. 2357–2359 (1982).] Serum antibodies obtained according to the published procedure were noted to be operative in neutralizing the antiviral biological effects of IFN-γ. While the capacity of antibodies to neutralize biological effects of macromolecules is in some instances considered to be an advantageous characteristic, this is not uniformly the case. As one example, neutralizing antibodies are of limited use in studies directed to elucidation of target cell receptor structure and function. More significantly, use of neutralizing antibodies in affinity purification procedures (wherein products are often isolated by quite harsh elution processes from bound association with fixed antibody preparations) may result in loss of biological activity of the purified material through disruption of "active" sites overlapping sites where binding to the antibody takes place.

There continues to exist a need in the art, therefore, for monoclonal antibodies which are specifically immunoreactive with IFN-γ. In order to meet the needs of the art, monoclonal antibody preparations would advantageously be immunoreactive with native and recombinant IFN-γ and analogs thereof, would also be immunoreactive with synthetic peptides substantially duplicative of IFN-γ, and would preferably be non-neutralizing of IFN-γ biological activity.

BRIEF SUMMARY

The present invention provides, for the first time, monoclonal antibody preparations which are specifically immunoreactive with IFN-γ and also specifically immunoreactive with polypeptide substances having amino acid sequences substantially duplicative of sequences extant in IFN-γ. Moreover, preferred antibodies provided by the invention are not operative to neutralize antiviral activity of IFN-γ.

In one of its aspects, the present invention provides a new mouse-mouse hybridoma cell line A.T.C.C. No. HB8291. This cell line secretes into the media as a product of its growth a highly specific monoclonal, anti-IFN-γ antibody which is also specifically immunoreactive with a polypeptide comprising the following sequence of amino acids: NH₂-Lys-Thr-Gly-Lys-Arg-Lys-Arg-Ser-Gln-Met-Leu-Phe-Arg-Gly-Arg-Arg-Ala-Ser-Gln-COOH. The antibody produced by A.T.C.C. HB8291 is thus the first antibody substance ever demonstrated to be immunoreactive with both IFN-γ and a polypeptide substantially duplicative of the amino acid sequence extant in IFN-γ. Tumor cell line, A.T.C.C. HB8291, was deposited at the American Type Culture Collection, 12301 Parklawn Drive, Rockville, Md. 20852 on Apr. 12, 1983 and will become available to the public upon the issuance of a patent.

According to the invention the IgG1 antibody produced by A.T.C.C. HB8291 is advantageously employed in immunological procedures for the isolation of large quantities of pure, biologically active, naturally-occurring and recombinant IFN-γ and IFN-γ analogs (hereafter "IFN-γ products") and in diagnostic immunoassays for the quantitative detection of IFN-γ products in fluid samples, preparative gels and the like.

The antibody substances provided by the invention facilitate performance of assays for quantitative detection of IFN-γ products in fluid samples (including blood and other body fluids), especially those assays which require the use of two antibodies which are immunoreactive with two different antigenic determinants of IFN-γ products. In such procedures, a first antibody (e.g., that produced by A.T.C.C. No. HB8291) is immobilized on a solid support and, when contacted with the sample fluid, immunobinds to one antigenic determinant of the IFN-γ product in the fluid. A second antibody (e.g., a polyvalent, serum-derived antibody such as described in Johnson, et al., supra) which may be linked to a detectable label (or is subsequently detected with a labelled material) is contacted with the complex of IFN-γ and the first antibody and binds to a different antigenic determinant thereof. The quantity of IFN-γ products in the sample is thereafter determined through quantification of the bound second antibody.

Antibodies of the present invention also provide materials useful in performance of "competitive" solid or liquid phase assays for detection of IFN-γ products which involve use of two species of antigen (e.g., labelled and unlabelled) forms. (Analytical methods of this type are disclosed in the aforementioned U.S. patent application Ser. No. 463,724 by Egrie and specifically exemplified by erythropoietin detection procedures. The disclosures of said application are specifically incorporated by reference herein.) In such assays, for example, the quantity of IFN-γ products in a sample may be determined by the extent of competition for binding to the monoclonal antibodies with a labelled or immobilized synthetic peptide. Antibodies of the invention can also be expected to find use in affinity purification procedures of the aforementioned U.S. patent application Ser. No. 463,724, wherein differential affinity of a monoclonal antibody for a proteinaceous macromolecule and for a synthetic peptide allows the displacement elution of a desired material from bound association with an immobilized antibody.

In another aspect of the invention, antibodies of the invention provide for the rapid determination of expression of IFN-γ products by microorganisms.

Other aspects and advantages of the invention will be apparent upon consideration of the following detailed description of preferred embodiments thereof.

DETAILED DESCRIPTION

The following examples illustrate practice of the invention in the production of hybridoma cell line A.T.C.C. No. HB8291 and the isolation of monoclonal antibodies to both IFN-γ products and a nonadecapeptide (19-mer polypeptide) duplicative of sequences of amino acids extant in IFN-γ at its carboxy terminal. Also illustrated is the characterization, amplification and determination of properties of antibodies produced by A.T.C.C. No. HB8291.

EXAMPLE 1

Development of Amino Acid Sequences and Synthetic Peptide

Review of the published sequence of IFN-γ noted above revealed the following sequences of amino acids which, according to analysis by the general procedures of Hopp, et al., *P.N.A.S. (U.S.A.)*, 78, p. 3824 (1981) appear to have significant antigenic potential independently of association with the entire IFN-γ glycoprotein:

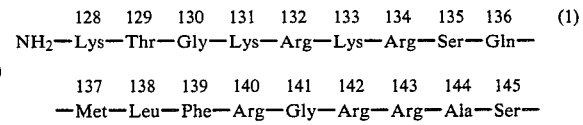

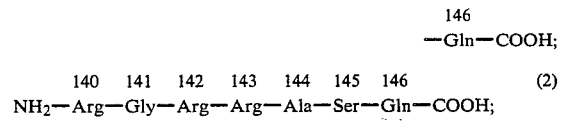

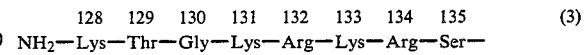

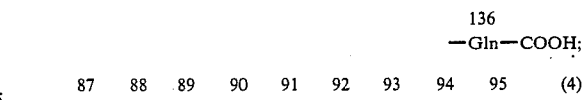

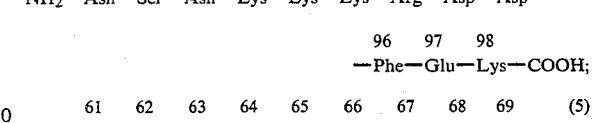

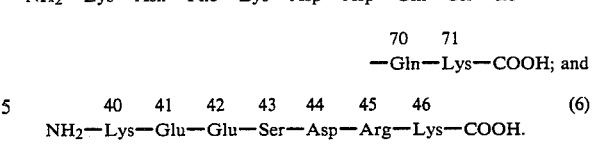

The sequence of amino acids spanning residues 137 through 139 (Met-Leu-Phe) is significantly hydrophilic and hence likely to have substantial antigenic potential and on this basis the 19-mer of sequence No. 1 was selected for initial studies.

A synthetic replica of the above-noted 19-mer sequence No. 1 was prepared according to the procedure of [Merrifield, R. B., *J. of Am. Chem. Soc.*, 85, 2149–2154 (1963)] [see also, Stewart, J. M., et al., *Solid Phase Peptide Synthesis*, San Francisco: W. H. Freeman & Co. (1969)] and covalently crosslinked using glutaraldehyde to a keyhole limpet hemocyanin (KLH) carrier protein, according to the procedure of Baron, et al., *Cell*, 28, pp. 395–404 (1982).

EXAMPLE 2

Hybridoma Production

In the procedure for production of hybridoma cell line A.T.C.C. No. HB8291, BALB/c mice (Simonsen Laboratories, Gilroy, Ca.) were hyperimmunized to the KLH-bound synthetic polypeptide prepared according to Example 1. The immunization and cell fusion procedures were performed according to essentially standard procedures set out in Oi, et al., pp. 351–372 in *Selected Methods in Cellular Immunology* (Mishell, et al., eds.), W. H. Freeman Publishing, San Francisco (1979). The first inoculation was subcutaneous and contained 10 micrograms of crosslinked 19-mer synthetic peptide plus Difco H37Ra Complete Freund's Adjuvant (Difco Laboratories). Further inoculations were given intraperitoneally 7, 21 42, and 73 days after the subcutaneous injection, each containing 10 micrograms of crosslinked 19-mer synthetic peptide. Three days prior to cell fusion (on day 94), the mice were inoculated with a final intraperitoneal injection containing 10 micrograms of crosslinked 19-mer synthetic peptide.

After the third and fifth injections, serum from several mice was assayed by a solid phase binding radioimmunoassay tested positively for the presence of antibodies to both the synthetic peptide and to a lysate of *E. coli* cells harboring a vector including a manufactured DNA sequence coding for IFN-$\gamma$ products. Briefly put, a solid phase binding assay was developed using the synthetic peptide immobilized in Immucon wells (Dynatech Labs., Inc., Alexandria, Va.), dilutions of mouse anti-synthetic peptide antiserum and $I^{125}$ labelled rabbit anti-mouse immunoglobulin. This assay had the advantage of not requiring labelling (and hence possible chemical modification) of the peptide antigen. The above-noted bacterial lysate competed for binding.

Following verification that the inoculated mice were producing serum antibodies to IFN$\gamma$ products and the synthetic polypeptide, spleens of the five most responsive immunized BALB/c mice, which contain a small number of antibody-producing lymphocytes, were disrupted to single cells. In the presence of the fusogen polyethylene glycol, immune donor spleen cells are fused with a parental BALB/c myeloma cell line, SP2/0-[HPRT$^-$] [Schulman, et al., *Nature*, 276, 269 (1978)] to produce a variety of hybrids. Briefly described, cell membranes fuse and initially surround a common cytoplasm with two or more nuclei. Several days after that event, the nuclei fuse and become capable of synchronous mitosis. As these fused cells divide, a variable number of chromosomes of both fused partners are lost until the hybrid cell lines stabilize.

Fused cells are plated into 8 multiple 96-well plates (768 total wells) at from $10^5$ to $10^6$ cells per well. Selection of SP2/0:spleen cell hybrids from the fusion which also produces SP2/0:SP2/0 and spleen:spleen cell hybrids is accomplished by culturing the fusion mixture in hypoxanthine-aminopterin-thymidine (HAT) medium for two weeks. HAT medium prevents SP2/0:SP2/0 hybrids from dividing. The spleen:spleen cell hybrids generally die after two weeks in culture. Thus the HAT medium allows growth of only the SP2/0:spleen hybrid cells.

After 10 days, many of the 768 wells contained multiple, viable cell colonies. Thereafter the individual cell colonies were screened for the presence of immunoglobulins and IFN-$\gamma$-specific antibodies.

EXAMPLE 3

Screening, Cloning and Characterization of Monoclonal Antibodies

A radioimmunoassay as in Example 2 was performed to reveal specific anti-IFN-$\gamma$, anti-polypeptide antibodies in the wells. Based on the results of these two screening assays, 14 of the 768 initial wells, positive for anti-polypeptide antibody and IFN-$\gamma$, were selected for minicloning.

Cells from each of the initially screened colonies were further subdivided into several multiwell plates (about ten cells per well), and allowed to grow. These wells were again screened by radioimmunoassay for the presence of both anti-polypeptide and anti-IFN-$\gamma$ antibody.

Cells from the 6 strongest positive miniclone wells were selected for formal cloning and diluted into new plates at a calculated density of 1 cell per 3 wells. The low density assures that a high proportion of colonies will derive from a single cell. Monoclonal proliferation of cells was screened periodically by microscopic examination. Thereafter culture fluids from all wells were assayed by radioimmunoassay in the procedures described above. The results of this cloning procedure produced 130 positive wells, of which the 45 most positive were further propagated. From these, ten presumptively equivalent, strongly positive single-cell colonies producing antibody to both the polypeptide and IFN-$\gamma$ and having satisfactory cell growth rate and density were selected. All colonies produced on the order of 100 micrograms of antibody per milliliter of culture fluid. One of these 10 cell lines was selected for deposit as A.T.C.C. No. HB8291.

To isolate maximum antibody producing cells, A.T.C.C. No. HB8291 cells are continuously subcultured to avoid deleterious effects of aging. A desirable medium for growth of hybridoma cells is HB101 (Hanna Biologicals) supplemented with 1% fetal calf serum (Tissue Culture Biologicals); when cells are in condition for harvesting culture fluid, the medium is preferably changed to HB101 without fetal calf serum.

Monoclonal antibodies may be isolated from culture fluids by AMICON filtration concentration (Amicon), followed by precipitation with 45% ammonium sulfate. Alternatively, the concentrated culture fluids may be adsorbed to Protein A-Sepharose columns (Pharmacia Corp.). [See, Goding, *J.Imm.Methods*, 39, 285–308 (1980)]. In these columns, the Protein A attaches to the Fc portion of the antibody immunoglobulin, allowing other contaminants in the culture fluid to elute out of association with the antibody. Although column capacity for mouse IgG1 is low, nonetheless, the antibody achieves considerable purification by this method.

To obtain a more concentrated antibody than that produced in tissue culture, the monoclonal antibodies of the present invention may be amplified by the ascites method generally described in Kenneth, et al., (eds.), *Monoclonal Antibodies, Hybridomas: A New Dimension in Biological Analysis*, p. 403, New York: Plenum Press (1981). According to this procedure, $10^6$ hybridoma cells may be injected into the peritoneal cavities of BALB/c mice, previously treated with 0.50 ml Pristane (Aldrich Chemical Co.). Pristane treatment promotes growth of tumor cells in an ascitic form within the peritoneal cavity. Once the ascitic tumor cells grow, the mice are sacrificed and the ascitic fluid containing the monoclonal antibody is harvested from the cells by centrifugation. The monoclonal antibody in the ascites fluid is then assayed for antibody titer. Ascites fluids containing on the order of 10 milligrams of IgG antibody per milliliter of culture fluid have been obtained by this method. Ascites fluid antibodies can be further purified from ascites fluid albumin by 45% ammonium sulfate precipitation and ion exchange chromatography.

Monoclonal antibody preparations were derived by purification from ascites fluids with Protein-A sepharose as described above for culture fluid purification. These isolates were radioiodinated using the chloramine T by the general method of Hunter, et al., *Nature*, 194, pp. 495–496 (1962). The $I^{125}$-labelled products retained their prior immunological activity in the radioimmunoassay.

Competitive binding experiments using ascites fluid-derived radiolabelled antibodies were employed to evaluate epitope specificities of the antibodies and indicated that all ten monoclone products (including that produced by A.T.C.C. HB8291) recognized the same (or, at least a closely adjacent or overlapping) epitope on the synthetic peptide.

EXAMPLE 4

Western Blot Assays For Microbially-Expressed IFN-γ Products

The value of monoclonal antibody preparations according to the invention as research tools is exemplified by their use in "Western Blot" analyses [see, Burnett, *Anal.Biochem.*, 112, pp. 195–203 (1981)] of cellular extracts of microorganisms wherein synthesis of recombinant IFN-γ and IFN-γ analogs is attempted.

The following general procedures were employed in those analyses. Crude extracts of *E. coli* cells which had been transformed with plasmid DNA coding for IFN-γ and IFN-γ analogs (which differed IFN-γ in terms of the identity or location of one or more amino acids) were run on a standard SDS-PAGE gel with markers of varying molecular weights in an attempt to determine the presence of the desired polypeptide in the lysate. A nitrocellulose filter paper was placed over the gel and the gel was placed in a liquid electrophoretic cell in order to transfer the protein bands to the filter paper. The paper was "blocked" by treatment with 5% bovine serum albumin. The paper was then treated with a monoclonal antibody solution containing approximately 100 micrograms/ml antibody. Specific immunoreactivity of the antibody with the recombinant IFN-γ or IFN-γ analog allowed autoradiographic visualization of the presence of antibody bound to desired product upon treatment with radioiodinated rabbit anti-mouse IgG antisera.

EXAMPLE 5

Neutralization Studies

A study was conducted for the purpose of comparing the effects of various antibody preparations on the antiviral biological activity of IFN-γ. The general procedure was patterned on Research Reference Reagent Note 22 accompanying sheep antiserum to human leukocyte interferon, N.I.A.I.D. Catalog No. G-026-502-568. In this procedure, a standard quantity of commercially prepared IFN-γ ($2 \times 10^3$ U/ml) was incubated for three hours prior to incorporation with each of the following antibody preparations: (1) mouse antipeptide antiserum; (2) rabbit anti-peptide antiserum; (3) monoclonal antibody of twenty separate formal clones of Example 3; and rabbit anti-IFN-γ antiserum (Interferon Sciences New Brunswick, N.J.). The results of this procedure, applied to WISH cells challenged with encephalomyocarditis virus (EMCV), are set out in Table I.

TABLE 1

| ANTIBODY | FINAL DILUTION | % NEUTRALIZATION |
|---|---|---|
| Mouse anti-IFN-γ peptide | 1:20 | 0 |
| Rabbit Anti-IFN-γ peptide | 1:20 | 0 |
| Mouse Anti IFN-γ Peptide Monoclones (e.g., HB8291) | 1:2 | 0 |
| Interferon Sciences rabbit Anti-IFN-γ | 1:10–1:20 | 92–96 |

The monoclonal antibodies of the present invention, while specifically immunoreactive with naturally-occurring IFN-γ, do not operate to neutralize the antiviral activity of this interferon.

EXAMPLE 6

Isolation of IFN-γ Products By Affinity Purification

Initial studies are being conducted relating to the utility of monoclonal antibodies of the invention in the affinity purification of IFN-γ products including naturally-occurring IFN-γ, recombinant IFN-γ and analogs of IFN-γ produced by recombinant procedures. In a first series of tests, monoclonal antibodies according to Example 3 were immobilized on Affi-gel 10 (BIORAD, Richmond, CA.) and employed as an affinity absorbent for crude cell extracts of microorganisms genetically transformed to express analogs of IFN-γ. Alkaline elution using 0.1 M diethylamine, pH 11.5 resulted in the isolation of microgram amounts of highly purified [$Lys^{81}$]IFN-γ. A column of cyanogen bromide activated Sepharose (Pharmacia) containing immobilized monoclonal antibody preparations of the invention for use in large scale isolations was constructed and employed to secure nearly milligram amounts of recombinant IFN-γ analogs from bacterial extracts. As previously noted, it is expected that highly purified biologically active IFN-γ products will be isolatable through use of synthetic peptides to elute desired products from bound association with monoclonal antibodies of the invention by means of differential affinity. Preliminary binding affinity assays indicate that, e.g., the antibody produced by A.T.C.C. HB8291 has a somewhat higher affinity for the above-noted 19-mer than for naturally-occurring IFN-γ. While the synthetic 19-mer employed in "raising" the antibodies produced by HB8291 is currently the material of choice for use in such procedures, it is anticipated that other polypeptides which duplicate only a portion of the 19-mer's sequence (e.g., polypeptide Nos. 2 and/or 3 of Example 1) may also be useful.

Monoclonal antibodies of the invention may be suitably employed in labelled or unlabelled form for quantitative detection of IFN-γ products in any of the general immunological assay procedures (RIA's, ELISA's, and the like) presently employing antibody preparations. As previously noted, the fact that preferred antibodies of the invention are specifically immunoreactive with both IFN-γ products and synthetic peptides makes possible immunological quantification procedures involving two "antigens". Further, the fact that preferred antibody preparations are known to be specifically immunoreactive with a specific region of IFN-γ products allows the development of assays involving two or more antibodies which are individually reactive with differing epitopes. Finally, the fact that preferred antibody preparations of the invention are non-neutralizing makes possible the practice of IFN-γ detection procedures which do not interfere with biological activity. Such procedures are especially significant to further basic research in the characterization of cell surface IFN-γ receptors.

While the foregoing illustrative examples are specifically directed to the present invention as exemplified by the development of cell line A.T.C.C. HB8291 and monoclonal antibody preparations derived therefrom, it will be understood that the contributions of the present invention are not limited thereto. The monoclonal antibodies provided by the invention are believed to be the first substances ever isolated which are specifically immunoreactive with IFN-γ products. They are also believed to be the first such substances which are specifically immunoreactive with a synthetic polypeptide which duplicates amino acid residues extant in IFN-γ. Finally, the monoclonal antibodies provided by the invention are the first anti-IFN-γ antibody materials ever available which do not neutralize IFN-γ antiviral activity.

Numerous modifications and variations in practice of the invention are expected to occur to those skilled in the art upon consideration of the foregoing description of presently preferred embodiments thereof. As one example, while the examples generally refer to the use of synthetic peptides which duplicate the nineteen carboxyl terminal amino acids of IFN-γ, it will be understood that the use of elongated or abbreviated polypeptides duplicating all or only an immunologically significant portion of the specified 19-mer are contemplated, as are polypeptides including a [Gln$^{140}$] residue rather than an [Asp$^{140}$] residue. With respect to the last-mentioned factor, it is noteworthy that the antibody of A.T.C.C. HB8291 appears to be immunoreactive with commercial IFN-γ preparations which may include the [Gln$^{140}$] species as well as with recombinant IFN-γ and IFN-γ analog products, all of which included an asparagine residue at position 140. Consequently, only such limitations should be placed upon the scope of the invention as appear in the appended claims.

What is claimed is:

1. As a new composition, a murine-derived hybridoma cell line ATCC HB8291 capable of producing in the medium of its growth an IgG monoclonal antibody capable of specifically binding to human IFN-γ in an antigen-antibody complex.

2. As a new composition, the monoclonal antibody produced from hybridoma cell line ATCC HB8291, said antibody capable of specifically binding to human IFN-γ.

3. In an immunological procedure for isolation of biologically active human IFN-γ or polypeptide analogs thereof from a biological fluid comprising the steps of contacting IFN-γ or polypeptide analogs thereof with an antibody specific for IFN-γ for a time and under conditions sufficient for formation of an immune complex of said IFN-γ or polypeptide analogs thereof and said antibody specific for IFN-γ and isolating said IFN-γ or polypeptide analogs thereof from said immune complex, the improvement comprising:

employing as said specific antibody an IgG monoclonal antibody produced by a murine-derived hybridoma cell line deposited as ATCC No. HB8291, said antibody capable of specifically binding to human IFN-γ in an antigen-antibody complex.

4. In an immunological procedure for the quantitative detection of IFN-γ or a polypeptide analog thereof, from a biological fluid comprising the steps of contacting IFN-γ or polypeptide analogs thereof with an antibody specific for IFN-γ for a time and under conditions sufficient for formation of an immune complex of said IFN-γ or polypeptide analogs thereof and said antibody specific for IFN-γ and detecting the presence of said immune complex, the improvement comprising:

employing as said specific antibody of IgG monoclonal antibody produced by a murine-derived hybridoma cell line deposited as ATCC No. HB8291, said antibody capable of specifically binding to human IFN-γ in an antigen-antibody complex.

* * * * *